US011320373B2

(12) United States Patent
Schneiderman et al.

(10) Patent No.: US 11,320,373 B2
(45) Date of Patent: May 3, 2022

(54) SYSTEMS AND METHODS FOR IDENTIFYING AND TREATING BIOLOGICAL MATERIALS

(71) Applicants: Jacob Schneiderman, Kiryat Ono (IL); Moshik Cohen, Neve Savion Or Yehuda (IL)

(72) Inventors: Jacob Schneiderman, Kiryat Ono (IL); Moshik Cohen, Neve Savion Or Yehuda (IL)

( * ) Notice: Subject to any disclaimer, the term of this patent is extended or adjusted under 35 U.S.C. 154(b) by 803 days.

(21) Appl. No.: 15/769,070

(22) PCT Filed: Oct. 20, 2016

(86) PCT No.: PCT/IL2016/051137
§ 371 (c)(1),
(2) Date: Apr. 18, 2018

(87) PCT Pub. No.: WO2017/068586
PCT Pub. Date: Apr. 27, 2017

(65) Prior Publication Data
US 2018/0321149 A1  Nov. 8, 2018

Related U.S. Application Data

(60) Provisional application No. 62/244,756, filed on Oct. 22, 2015.

(51) Int. Cl.
| | | |
|---|---|---|
| G01N 21/552 | (2014.01) | |
| A61N 5/06 | (2006.01) | |
| A61B 5/00 | (2006.01) | |
| G01N 21/49 | (2006.01) | |
| G02B 5/00 | (2006.01) | |

(Continued)

(52) U.S. Cl.
CPC ......... *G01N 21/554* (2013.01); *A61B 5/0066* (2013.01); *A61B 5/0084* (2013.01); *A61B 5/441* (2013.01); *A61N 5/0601* (2013.01); *A61N 5/062* (2013.01); *A61N 5/0625* (2013.01); *B82Y 30/00* (2013.01); *G01N 21/49* (2013.01); *G02B 5/008* (2013.01); *A61N 5/067* (2021.08); *A61N 2005/0632* (2013.01); *A61N 2005/0659* (2013.01); *A61N 2005/0662* (2013.01);
(Continued)

(58) Field of Classification Search
None
See application file for complete search history.

(56) References Cited

U.S. PATENT DOCUMENTS 8,802,154 B2 * 8/2014 Harris ................. A61K 8/11
424/489
2004/0155184 A1   8/2004 Stockman et al.
(Continued)

FOREIGN PATENT DOCUMENTS

EP         2133688 A1    12/2009

*Primary Examiner* — Yi-Shan Yang
(74) *Attorney, Agent, or Firm* — Soroker Agmon Nordman

(57) ABSTRACT

A system for identifying and optionally treating biological material is provided. The system includes a coherent light source for irradiating the biological material and device for collecting light waves reflected from the biological material and transforming the light waves to nanoplasmonic waves. The system also includes a processing module for extracting phase and amplitude information from the nanoplasmonic waves to identify the biological material based on the phase and amplitude information.

14 Claims, 18 Drawing Sheets

(51) Int. Cl.
*B82Y 30/00* (2011.01)
*A61N 5/067* (2006.01)

(52) U.S. Cl.
CPC ............ *A61N 2005/0663* (2013.01); *G01N 2201/06113* (2013.01)

(56) References Cited

U.S. PATENT DOCUMENTS

| | | | |
|---|---|---|---|
| 2011/0014473 A1* | 1/2011 | Ying | G01N 33/54346 428/407 |
| 2011/0021970 A1 | 1/2011 | Vo-Dinh et al. | |
| 2011/0058164 A1 | 3/2011 | Zhang et al. | |
| 2012/0029326 A1 | 2/2012 | Kawamura et al. | |
| 2012/0184047 A1* | 7/2012 | Jonsson | B01D 71/022 436/164 |
| 2012/0281957 A1* | 11/2012 | Chamanzar | G02B 6/12007 385/131 |
| 2012/0287429 A1* | 11/2012 | Van Dorpe | G02B 6/1226 356/301 |
| 2013/0148194 A1* | 6/2013 | Altug | G02B 5/008 359/350 |
| 2014/0104606 A1* | 4/2014 | Shih | B22F 9/16 356/301 |
| 2014/0342427 A1* | 11/2014 | Lee | C12N 13/00 435/173.1 |
| 2015/0177150 A1 | 6/2015 | Rothberg et al. | |
| 2016/0008492 A1* | 1/2016 | Mao | A61K 49/1845 424/9.322 |

\* cited by examiner

```
┌─────────────────────────────────────────┐
│   Excitation of the examined samples with laser │
│       light with a specific frequency           │
└─────────────────────────────────────────┘
                    ⬇
┌─────────────────────────────────────────┐
│     The scattered light is coupled to           │
│    plasmonic efficiently modes at the           │
│    waveguides using the nanoantennas            │
└─────────────────────────────────────────┘
                    ⬇
┌─────────────────────────────────────────┐
│   A scanning probe microscope collects the plasmon │
│   modes, spatial FFT is performed on the plasmon   │
│   modes inside the waveguides to extract the effective │
│          plasmon wavelength and phase              │
└─────────────────────────────────────────┘
                    ⬇
┌─────────────────────────────────────────┐
│   The wavelength and phase are sample specific. │
│   Noise is canceled by interfering the information │
│          from several waveguides.               │
└─────────────────────────────────────────┘
```

FIG. 4A

FIG. 5
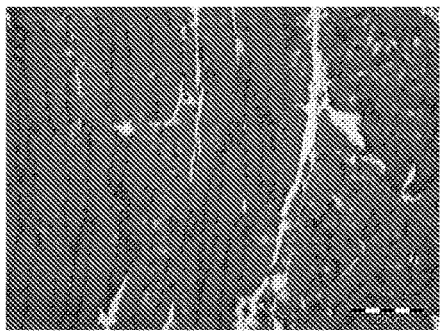 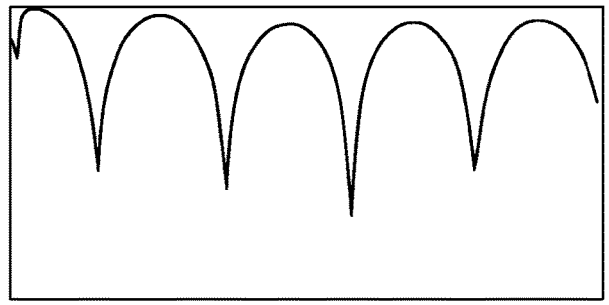
Normalized Intensity and scale are missing
FIG. 6
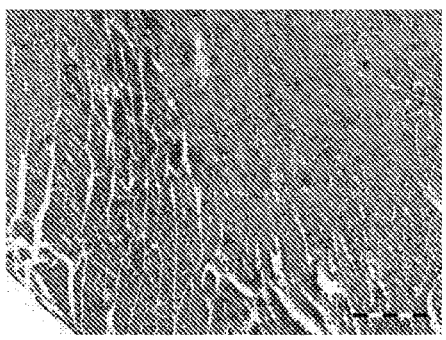 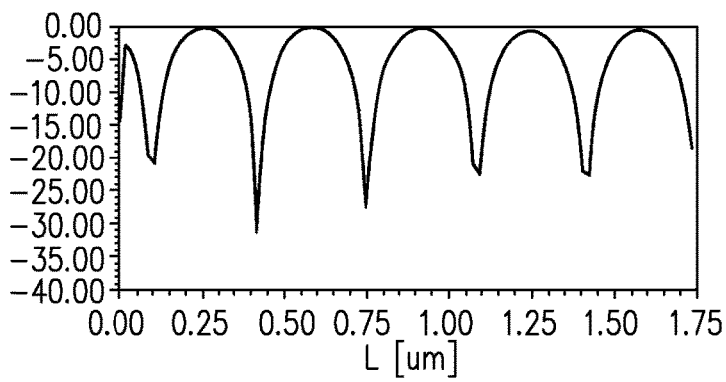
FIG. 7
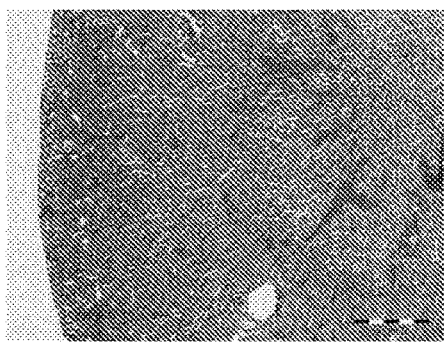 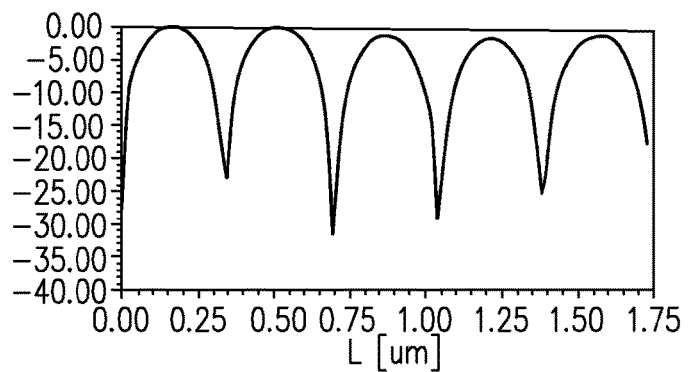

FIG. 8
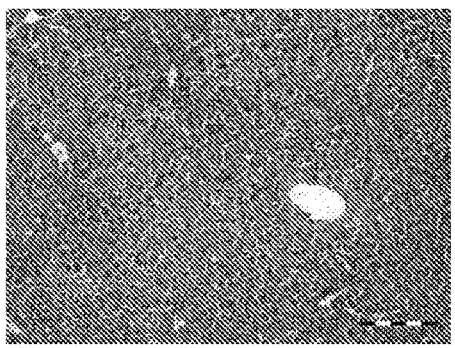 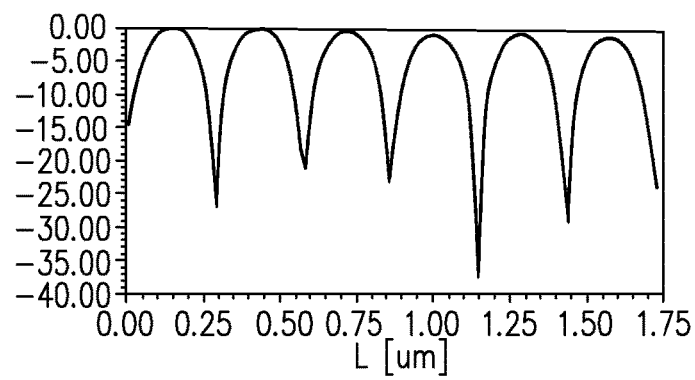
FIG. 9
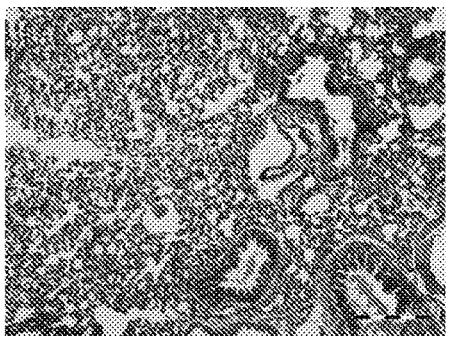 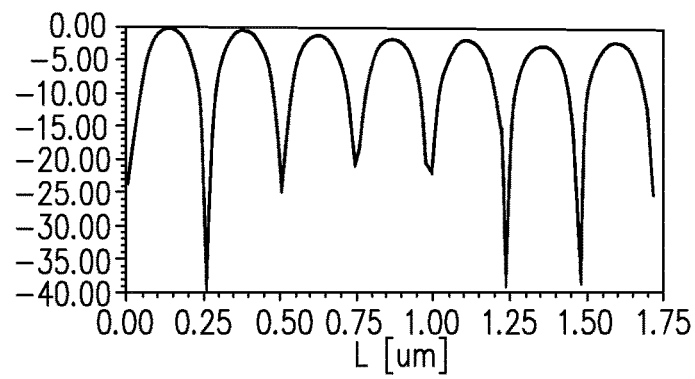
FIG. 10
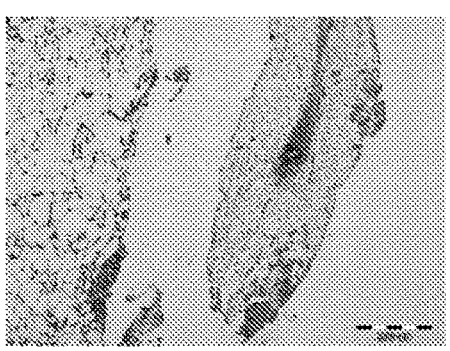 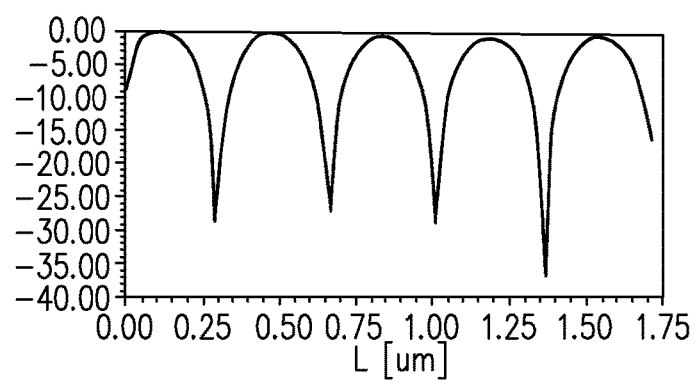

SYSTEMS AND METHODS FOR IDENTIFYING AND TREATING BIOLOGICAL MATERIALS

FIELD AND BACKGROUND OF THE INVENTION

The present invention relates to a system for identifying and optionally treating biological materials, including cells and tissues, and to a method of using the system in diagnostics and/or therapy. More particularly, the present invention relates to a system capable of identifying and characterizing biological material based on a plasmon/plasmon-polariton signature thereof.

Electromagnetic fields are commonly used in medicine for diagnosis and therapy. One emerging EMF technology that has potential medical applications is plasmonics.

Plasmonics is the study of the interaction between an electromagnetic field and free electrons in a metal. Most applications of plasmonics to date have relied on the interaction of light with the metallic structures, followed by detection of the light at the same wavelength that is reflected or scattered from the structures. For example, the optical excitation of surface plasmons in metal nanoparticles has led to the emerging field known as molecular plasmonics. Recent advances in molecular plasmonics and nanofabrication techniques have enabled novel optical materials and devices with applications in biology and nanomedicine.

While reducing the present invention to practice, the present inventor has discovered that surface plasmons and surface plasmon-polaritons collected from electromagnetic radiation reflected from biological materials (e.g., cells, tissues) can be used to identify and type the biological materials.

Thus, the present invention provides a system which is capable of identifying and typing biological material via plasmon/plasmon-polariton signature unique to the biological material.

SUMMARY OF THE INVENTION

According to one aspect of the present invention there is provided a system for identifying biological materials comprising (a) a coherent light source for irradiating the biological materials; (b) a device for collecting light waves reflected from the biological materials and transforming the light waves to propagating nanoplasmonic waves; and (c) a processing module for extracting phase and amplitude information from the nanoplasmonic waves and identify the biological material based on the phase and amplitude information.

According to further features in preferred embodiments of the invention described below, the coherent light source irradiates the biological sample with a light having a wavelength of 450 nm-10000 nm.

According to still further features in the described preferred embodiments the device includes one or more (e.g. an array) of plasmonic nanoantennas.

According to still further features in the described preferred embodiments the device further includes a plasmonic waveguide coupled to the at least one nanoantenna.

According to still further features in the described preferred embodiments the device includes a Silicon layer attached to Silicon Oxide layer.

According to still further features in the described preferred embodiments the nanoantenna is embedded within the Silicon Oxide layer.

According to still further features in the described preferred embodiments the nanoantenna is 400 nm×30 nm×30 nm size.

According to still further features in the described preferred embodiments the nanoantenna is fabricated from Gold, Silver or Aluminum.

According to still further features in the described preferred embodiments the nanoantenna is coated with a 2 nm-5 nm protective layer fabricated from a polymer.

According to still further features in the described preferred embodiments the waveguide is fabricated from a nanoplasmonic Metal-Insulator-Metal sandwich.

According to still further features in the described preferred embodiments the waveguide includes an insulative layer of air, Silicone oxide, a polymer or a ceramic.

According to still further features in the described preferred embodiments the phase and amplitude information is extracted at a spatial resolution of 10 nm-1000 nm.

According to still further features in the described preferred embodiments the system further includes a nanometric phase shifter for controlling a phase of the light waves reflected from the biological material via electrostatic charging of the nanoantenna.

According to still further features in the described preferred embodiments the phase and amplitude information is utilized to sense and image the biological materials.

According to another aspect of the present invention there is provided a system for treating biological material comprising: (a) a light source for producing a coherent light beam: (b) a device for transforming the coherent light beam into nanoplasmonic waves; and projecting the nanoplasmonic waves onto the biological material thereby treating it.

According to still further features in the described preferred embodiments the nanoplasmonic waves are of a wavelength suitable for disrupting a cellular membrane.

According to another aspect of the present invention there is provided a method of identifying biological material comprising: (a) irradiating the biological material with coherent light; (b) collecting light waves reflected from the biological material and transforming the light waves to nanoplasmonic waves; and (c) extracting phase and amplitude information from the nanoplasmonic waves and identifying the biological material based on the phase and amplitude information.

According to still further features in the described preferred embodiments the coherent light has a wavelength of 450 nm-10000 nm.

According to still further features in the described preferred embodiments the phase and amplitude information is utilized to sense and image the biological material.

According to still further features in the described preferred embodiments (b) is effected by a device including nanoantenna coupled with a plasmonic MIM waveguide.

According to another aspect of the present invention there is provided a system for treating tissue comprising (a) a device for irradiating the tissue with an electromagnetic signal: and (b) a plurality of a nanoantenna particles each being linked to a chemical moiety targeted to the tissue and each being capable of undergoing plasmonic excitation when exposed to the electromagnetic signal.

According to still further features in the described preferred embodiments each of the nanoantenna particles further includes an agent being activatable to destroy the tissue when the nanoantenna particles are plasmonically excited.

According to still further features in the described preferred embodiments the electromagnetic signal is IR laser, visible laser or white light.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a-c schematically illustrate the arrangement of the nanoantenna elements (FIGS. 3a and c) and nanoantennas-waveguides (FIG. 3b) of the light collecting device of the present system. FIG. 3d is an electron micrograph of the nanoantennas used in the present studies; $L_{Arm}$=140 nm. $L_C$=120 nm, s=30 nm and g=6 nm. FIG. 3e illustrates a novel plasmonic nanoantenna design capable of a plasmonic response on a single nanometer scale.

FIGS. 5-10 illustrate the intensity map and plasmonic wave graph obtained from samples of different tissues, including peripheral muscle (FIG. 5), heart (FIG. 6), Kidney (FIG. 7), liver (FIG. 8), lung (FIG. 9) and fat tissue (FIG. 10).

DESCRIPTION OF THE PREFERRED EMBODIMENTS

Figure 1:
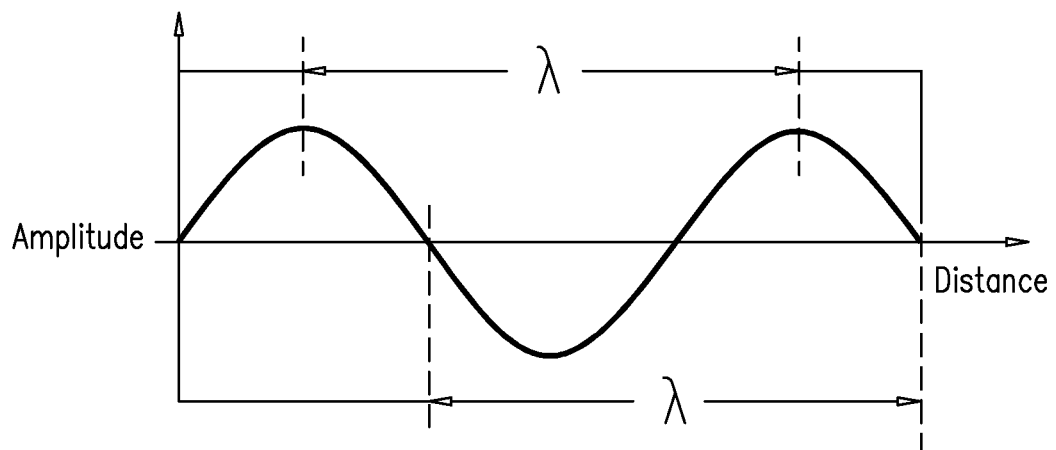
FIG. 1 is a graph illustrating the peak-to-peak distance and amplitude in a typical light wave.

The present invention is of a system which can be used to identify, type and treat biological material. Specifically, embodiments of the present invention can be used to identify pathological tissue or cells in vitro, or in vivo.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Use of plasmonics in medicine has been previously suggested. Studies have shown that surface plasmons emitted from metallic nanostructures can be used to enhance fluorescence of fluorophore [Plasmonics in Biology and Medicine III, edited by Tuan Vo-Dinh et al. Proceedings of SPIE Vol. 6099, 609909, (2006)] or to potentially treat cancerous tissue targeted by the metallic nanostructures (Rejiya et al. Pharmacological Research, 2011).

While experimenting with various antenna-waveguide devices for collection of surface plasmons and plasmon-polaritons, the present inventor has uncovered that nanoplasmonic interferometry, obtained at multiple Metal-Insulator-Metal (MIM) plasmonic waveguides can be used to type biological material such as molecules, cells and tissues.

As is described in the Examples section which follows, collection of surface plasmon-polaritons using multiple antenna-waveguide devices provides several advantages over surface plasmon resonance (SPR) detection approaches and greatly facilitates identification (presence/absence and location), typing and treatment of biological material such as molecules, cells and tissues.

The present system can be used for in-situ or in-vivo localization, qualification and quantitation of biological material related to pathologies (e.g. abnormal cells, plaques, pathological organisms such as bacteria, viruses and the like).

As is further described hereinunder, the present system is configured for establishing multiple plasmonic wave patterns that are sensitive to nano metric changes in a detected volume. The system includes a miniaturized optical wave source which illuminates a volume using safe, low power electromagnetic radiation. The volume-reflected beams are subsequently transformed to nanoplasmonic waves with a complex mode diffraction pattern. Such a diffraction pattern is characterized by phase and amplitude information with spatial resolution on the order of 1-10 nm. When a detectable object (e.g., cell or a molecular structure) is present in the irradiated volume, a change in the diffraction/wave pattern characteristic of the object is observed.

Thus, according to one aspect of the present invention there is provided a system for identifying biological material. The system can be used to detect, identify and quantitate any biological material in any setting (in-vitro, in-situ and in-vivo). Examples of biological material include normal and abnormal cells, and tissues.

The system of the present invention includes a coherent light source for irradiating a volume that includes a biological material. The light source can produce electromagnetic radiation which can penetrate the biological material to a depth of 1 um-5 cm. Examples of suitable light sources include He—Ne, Nd-Yag and preferably Er-Yag lasers, with preferable wavelengths at or near IR at milliwatt power levels. White light, or other broadband sources can also be used by the present invention but such light requires additional processing power.

The present system also includes a device which is capable of transforming the light waves reflected from the interrogated volume to nanoplasmonic waves. Such a device can be a Plasmonic chip, which includes an array of nano-metallic devices (antennas coupled to waveguides) fabricated on a standard silicon (Si) wafer. An example of such a device is described in greater detail hereinbelow with reference to FIGS. 2-3b.

The present system also includes a digital signal processor running a dedicated algorithm for extracting phase and amplitude information from the nanoplasmonic waves and identifying the biological material based on the phase and amplitude information. The phase and amplitude information extracted by the present system provide a signature which is tissue unique.

The wavelength and phase, which characterize the plasmonic mode, change as a function of the tissue type. Since the resolution of the present system is high (e.g. 20 nm) the present plasmonic technology identifies cells as well as subcellular structures. Identification of a tissue (tissue typing) depends on data related to the prevalence and spatial arrangement of different cellular components within the referenced volume. For each tissue, a specific plasmonic wave is excited, enabling detection of different tissues by excitation of different plasmons. For example, each wave period (the distance between two adjacent peaks) represents different plasmonic wavelength ($\lambda$) (FIG. 1). Therefore, specific peak distributions can be used to represent different types of tissues.

As is described in the Examples section, which follows, different tissues/cells exhibit different peak distributions, and each corresponds to a specific, plasmonic wavelength. For example, a muscle cell exhibits effective plasmonic wavelength of about 150 nm while a tumor cell exhibits a wavelength of about 170 nm.

By 'training' the present system against different tissue types, a specific signature can be correlated with each specific tissue type.

Once the present system is 'trained', it will be capable of identifying tissues solely based on the plasmonic signature.

Figure 2:
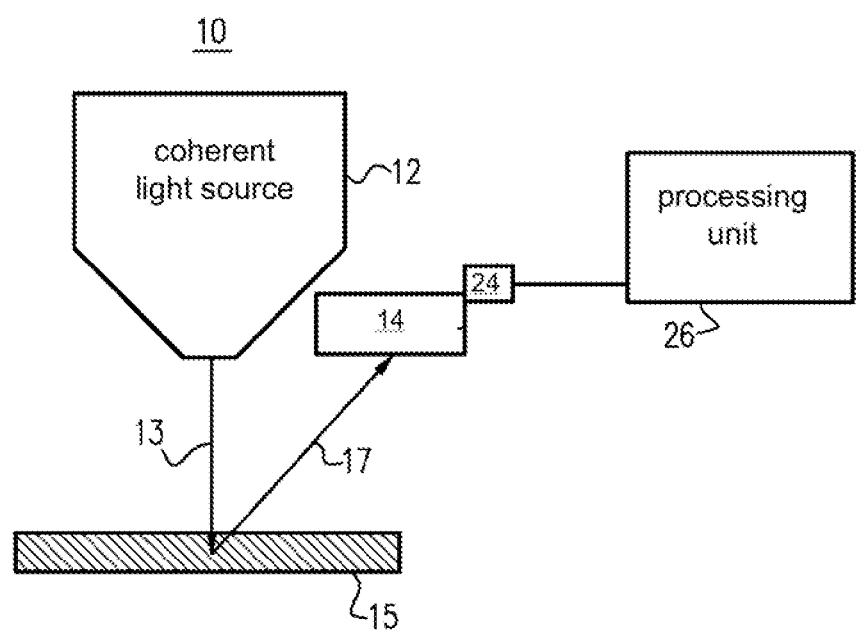
FIG. 2 illustrates the present system.

Referring now to the drawings, FIG. 2 illustrates one embodiment of the present system which is referred to herein as system 10.

System 10 includes a coherent light source 12 which is configured for directing a light beam 13 having a wavelength of 450 nm-10000 nm onto a volume 15 including the biological material (e.g., liquid suspension of cells or a tissue sample). Light source 12 can be an Er-Yag laser. Light source 12 can be used to probe or scan the volume. The beam scanning, can be performed mechanically via scanning probe or it can be done electronically via 2D materials as Graphene plasmonics phase shifters.

System 10 also includes a device 14 for collecting light waves 17 reflected from volume 15 and biological material contained therein.

Figure 3B:
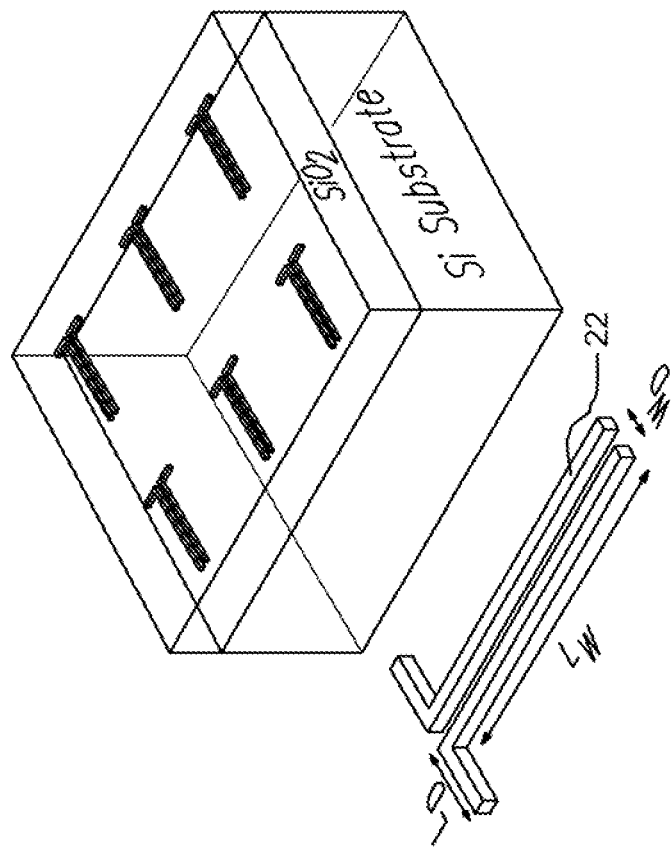
FIGS. 3a-e illustrate the nanoantennas and waveguides of the present invention.
Figure 3A:
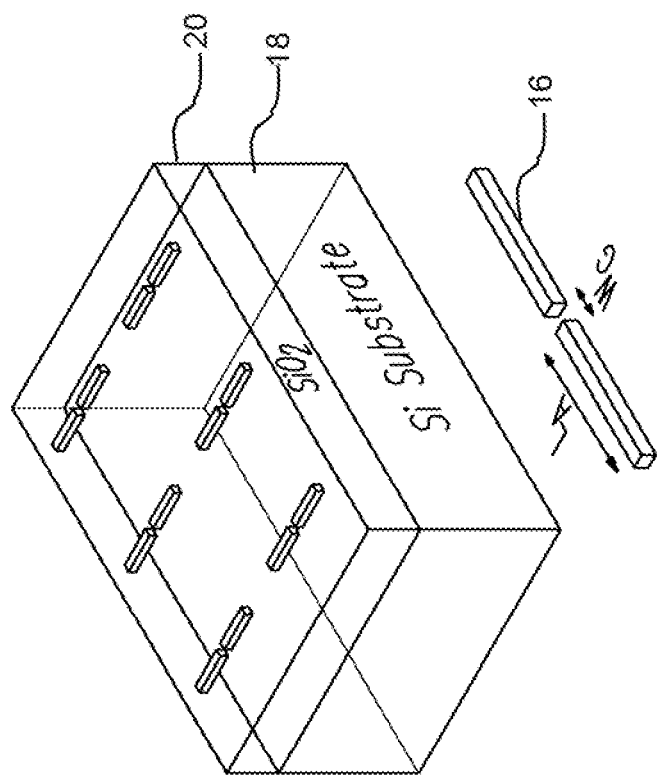

FIGS. 3a-b illustrate one embodiment of device 14 which is configured as a nanoantenna-waveguide array.

Device 14 includes nanoantenna elements 16 (FIG. 3a) sandwiched between a silicon layer 18 and a silicon Oxide layer 20. Any number of elements 16 can be used in device 14 (12 shown). Other configurations can include mechanical miniaturized motors or micro-mirror arrangements.

Elements 16 can be fabricated from gold, silver or aluminum (or combinations thereof) and configured as rectangles 400 nm×30 nm×30 nm in size. Additional shapes can be bowties and Yagi structures.

Elements 16 can be arranged as pairs (as shown in FIG. 2a) with a distance between pairs selected from a range of 150-1500 nm.

Elements 16 can be omnidirectional or directional antennas depending on the application requirements and system implementation.

Elements 16 can be coated with a 2-5 nm protective layer fabricated from a metal such as silver or gold.

Elements 16 are connected to waveguides 22 (FIG. 3b) to form a nanoantenna-waveguide construct. Waveguides 22 are arranged perpendicularly to elements 16 (as shown in FIG. 2b) or at any angle between 0-180 degrees. Waveguides 22 can be fabricated from a Metal-Insulator-Metal sandwich (e.g. Au-Air-Au) and are preferably rectangular in shape with dimensions of 1000 nm×50 nm×25 nm.

Waveguides 22 can include an insulative layer of air, silicone oxide, a polymer a ceramic or any type of dielectric material with positive relative permittivity.

Device 14 can also include a nano-metric phase shifter 24 (FIG. 2) for controlling the phase of light waves reflected from the biological material via electrostatic charging. A specific plasmonic phase shifter can be implemented by using an engineered layer of Graphene under each nanoantenna connected to a DC voltage source which facilitates the electrostatic charging upon voltage application.

The nanoantenna, schematically shown in FIG. 3a, is an engineered device including three closely spaced metallic (Gold) nanorods. Two identical nanorods of length LArm are separated by a nanoscopic gap (s=20 nm). A third nanorod, is positioned closer to the dipole (g=6 nm)). Fabrication was performed via electron beam lithography (EBL), ion beam sputtering (Ag, 20 nm) and liftoff with optimized beam doses. FIG. 3b shows a high-resolution scanning electron microscopy (HR-SEM) image of a fabricated nanoantenna, recorded at beam current of 0.5 nA and low accelerating voltage of 5 kV, for sub-nanometer imaging resolution. Nanoantenna with demotions of LArm=140 nm, LC=120 nm, s=30 nm and g=6 nm was fabricated. Moreover, as shown in FIG. 3b, the nano-arms and director can be fabricated with different widths. High-resolution nano-optical images were recorded while the devices are illuminated by a He—Ne laser at wavelength of 633 nm.

Figure 3C:
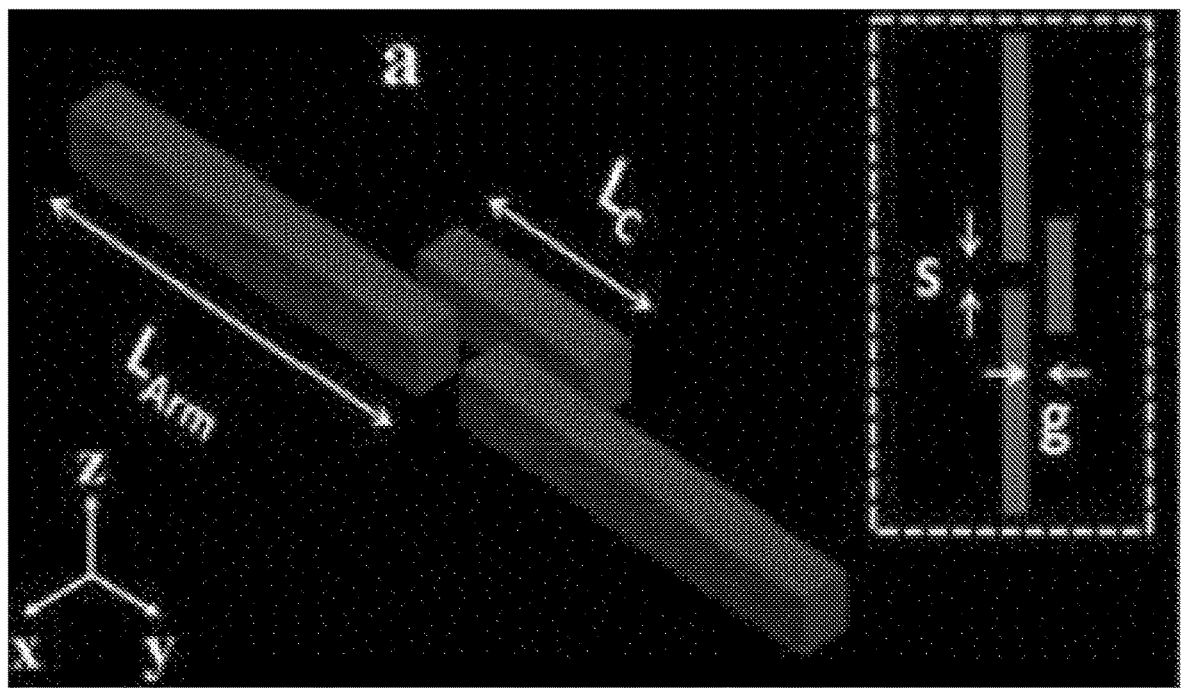

FIG. 3c shows high-resolution nano-optical mapping of a nanoantenna, recorded at s set lift height of 30 nm using high aspect ratio uncoated Si AFM tip with diameter of 2 nm. The numerical results are obtained using High Frequency Structure Simulator (ANSYS HFSS V15) based on the finite element method (FEM). Generally, the electric field is described by a 3D vector $E=(E_x, E_y, E_z)$, where each field component $E_i$ is characterized by both magnitude $|E_i|$ and phase $\phi i41$.

Figure 3D:
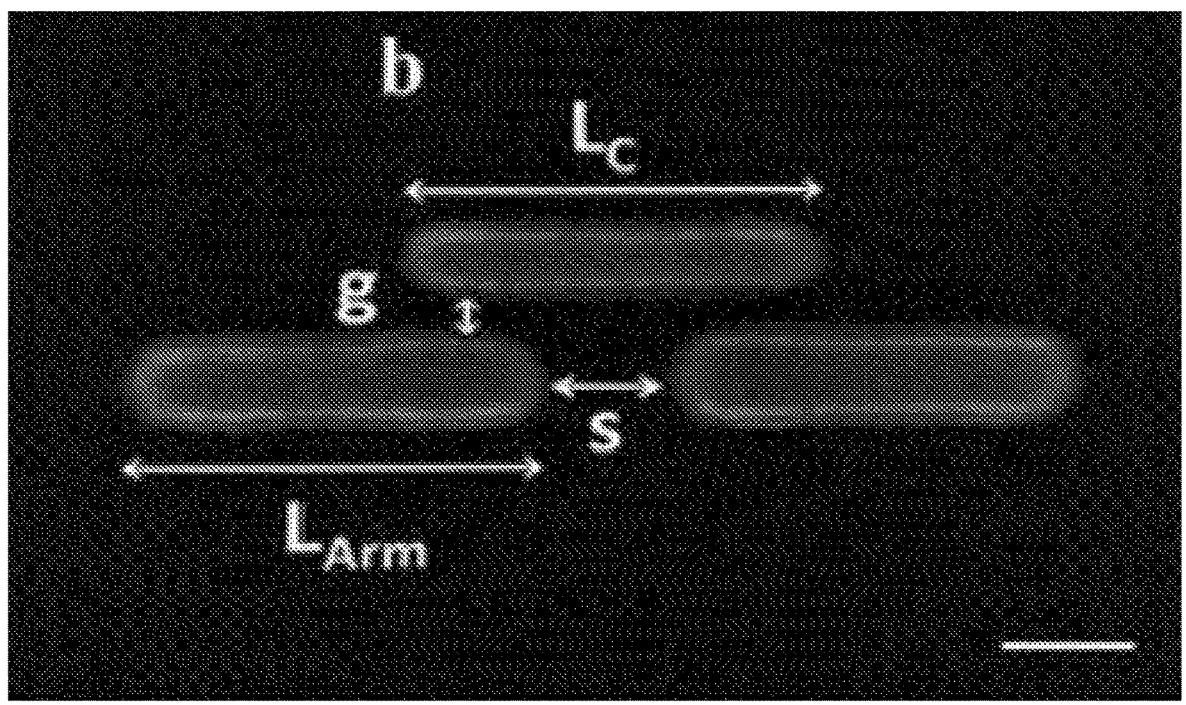
Figure 3E:
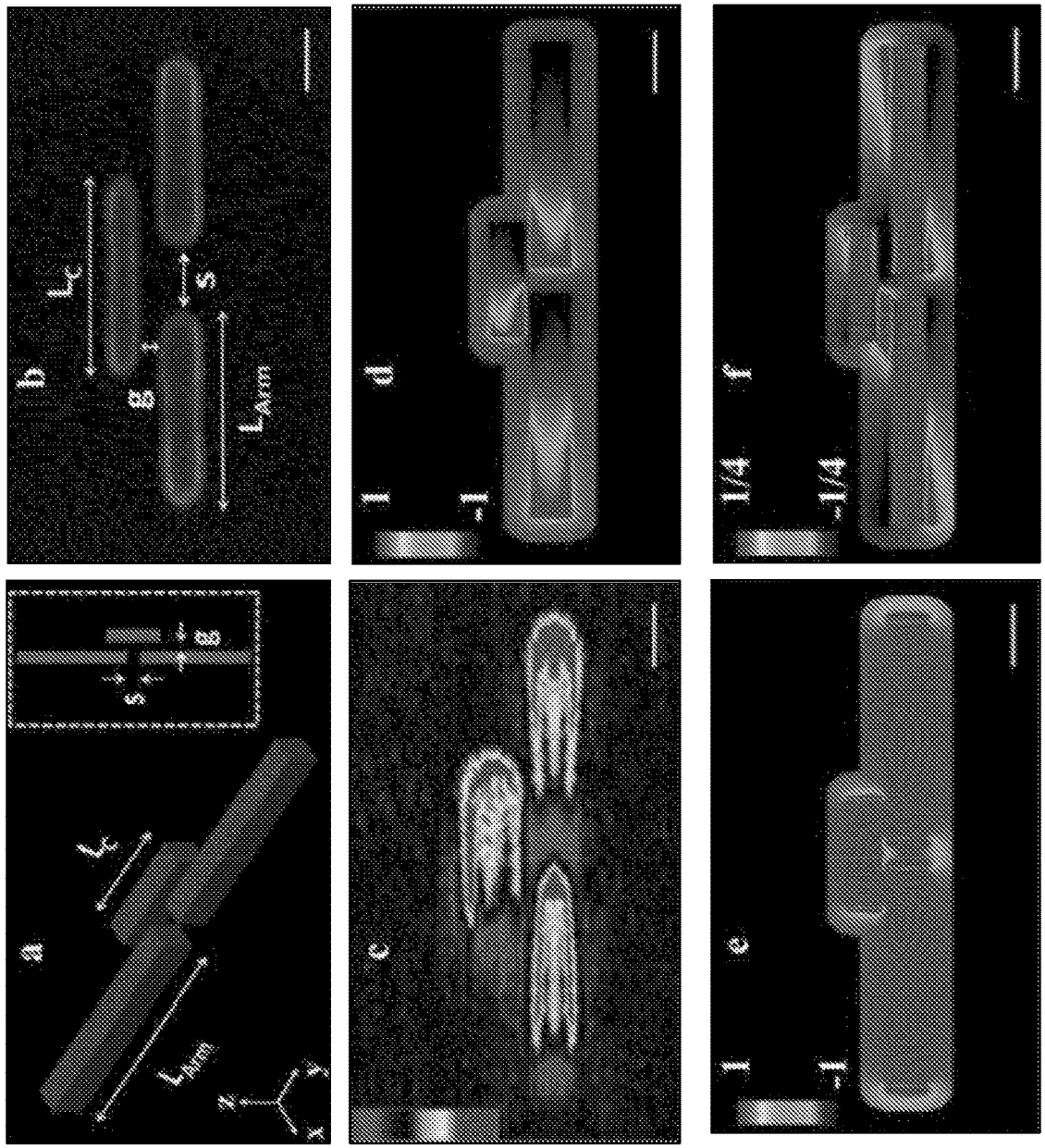

FIG. 3d shows the vertical near-field component $Re(E_z) = |E_z|cos(\phi z)$ where $|E_z|$ is the near-field amplitude and $\phi z$ the phase. The Ez field distribution appears very similar to the Nano optical map (FIG. 3c), exhibiting identical spatial phase distribution. FIGS. 3e and 3f show the Ex and Ey components (respectively) of the optical near fields.

Device 14 of system 10 functions as follows. Light reflected off the probed volume and biological material contained therein is converted by elements 16 (nanoantennas) to surface plasmons (SPs) and surface plasmon polaritons (SPPs) propagating at waveguide 22. The phase and period of these SPs and SPPs are strongly dependent on the probed sample. A nano-metric phase shifter tunes the received radiation pattern of nanoantennas 16 to achieve maximum array gain.

Figure 4A:
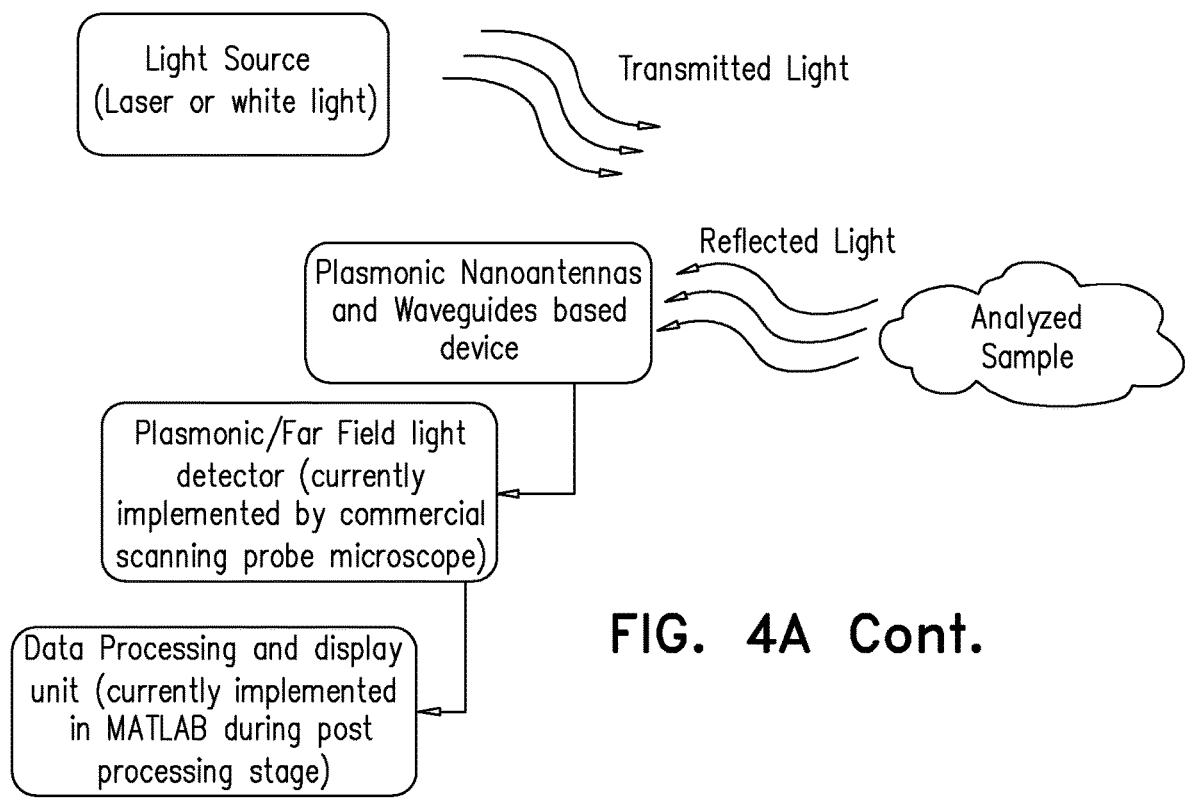
FIG. 4a is a flowchart outlining the processing steps for extracting a cell/tissue-specific plasmonic signature.

System 10 further includes a processing unit 26 (FIG. 2) for processing the light collected by device 14 and extracting the phase and amplitude information contained therein. The operation of processing unit 26 is summarized in the flow chart shown in FIG. 4.

The plasmonic signature derived by processing unit 26 can then be compared to a database of plasmonic signatures correlated with tissue/cell types to identify the tissue/cell present in the probed/scanned volume.

Figure 4B:
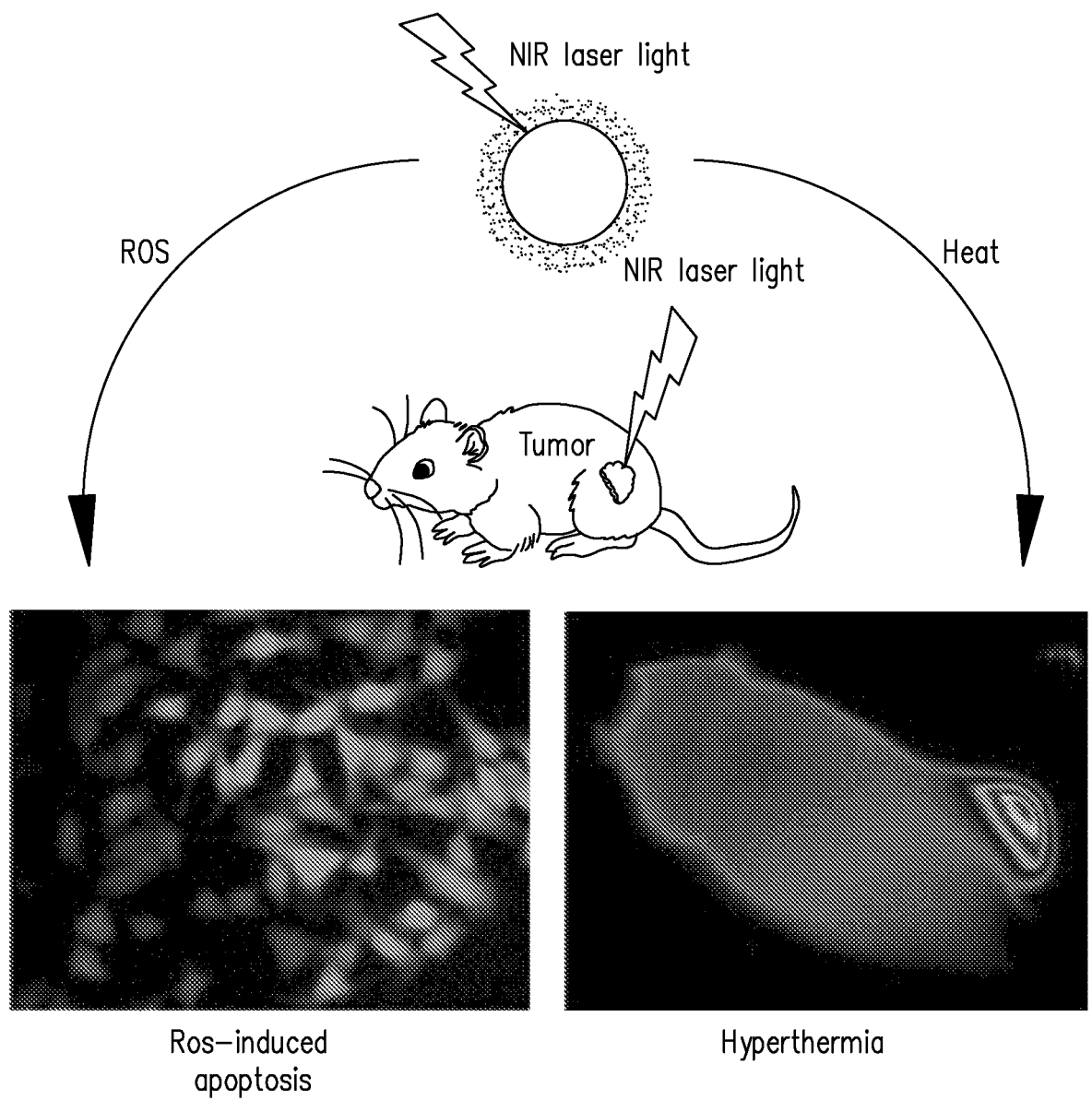
FIG. 4b illustrates use of plasmonic particles in photo thermal therapy (PTT) and photodynamic therapy (PTD).

System 10 of the present invention can be used for qualifying and quantifying biological material in sample or in-vivo and thus can be used in a variety of applications, including, but not limited to, identifying:

(i) normal cells and tissues;

(ii) abnormal cells, malignant and benign tumors and inflammation (including deep and superficial processes);

(iii) biological material associated with inflammatory processes, fibrosis, calcification and foreign body;

(iv) atherosclerotic plaques; and/or (v) "vulnerable plaques" (rupture prone plaques);

The present invention also encompasses use of a plasmonic beam system for treating biological tissue. Thus, according to another aspect of the present invention, there is provided a system for treating biological material. The system includes a light source for producing a coherent light beam and a device for transforming the coherent light beam into nanoplasmonic waves and projecting the nanoplasmonic waves onto the biological material thereby treating it. A typical system setup for performing photo therapy (thermal or light) is illustrated in FIG. 4b.

A plasmonic photo-thermal therapy (PTT) system can include a nano-device (Typical dimensions of ~500 nm×500 nm×200 nm) carrying nanoantennas (similar to those described above), that are chemically linked to targeting chemical moiety—a cell specific 'ligand' that is capable of binding to desired cells. For example, a nanoantenna array can be covalently linked to an antibody or antibody fragment capable of binding tumorous tissue or a cancer cell, a chemotherapeutic and/or radiosensitising agent such as mitomycin C or an amino acid sequence for targeting to a specific cell compartment (e.g. nucleus).

The nano device can further include any drug/prodrug for local drug release/activation upon plasmonic excitation or a resonant material (such as Au, Graphene, Al and Si) for increasing the plasmonic response of the nanoantenna array.

The nano-device is injected into a tissue, and diffuses to the specific tissue/cell targeted by the ligand. Upon illumination with a light source e.g. near IR laser, visible laser or a white light source), plasmonic resonance at the nanoantenna releases/activates the drug at the targeted cells or alternatively, the plasmonic resonance is amplified by the resonant material to generate a localized hot spot which thermally destroys the targeted cells.

Photodynamic therapy (PDT) is a similar approach which utilizes light instead of heat for treatment. This approach requires the use of a chemical compound—also known as photosensitizer—with a particular type of light to kill cancer cells. The photosensitizer in the tumor absorbs the light and generates reactive oxygen species (ROS)—such as hydroxyl radical, singlet oxygen, as well as peroxides—that destroy nearby cancer cells.

The present system can be embedded into a medical catheter and used as a tissue sensor in theranostics (diagnostic+therapeutic) applications. Such a catheter can further include a therapeutic unit for treating tissue via, for example, mechanical (cutting), thermal (RF ablation), cryogenic or photoactivation (e.g. PDT) modalities. Alternatively, system 10 can also be configured to also provide a therapeutic signal as is described hereinabove.

Figure 12:
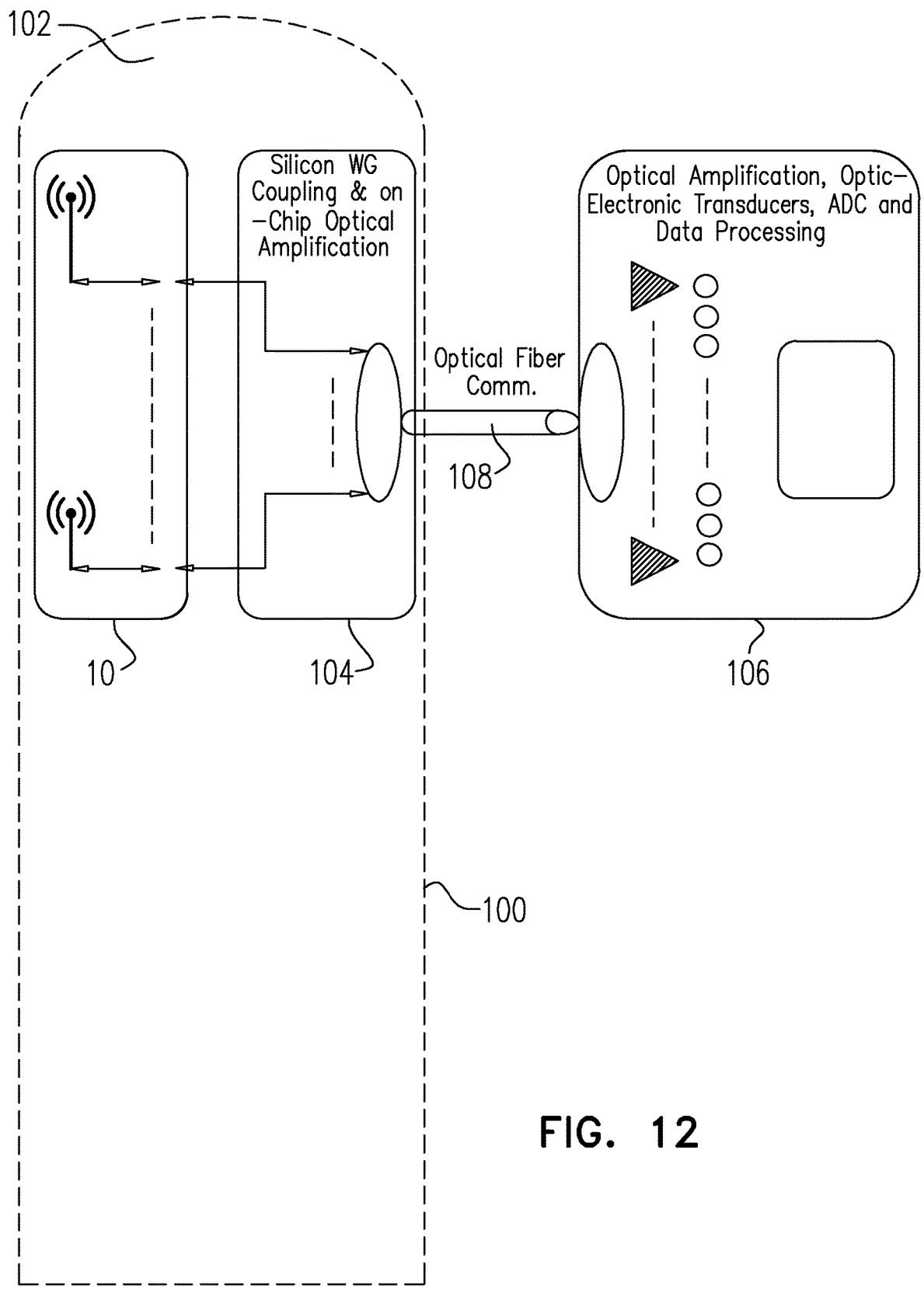
FIG. 12 illustrates a theranostic catheter which utilizes the present system as a sensor and optionally therapeutic unit.

FIG. 12 illustrates one embodiment of a catheter 100 which includes a system 10 sensor. System 10 is fabricated on a silicon chip which is integrated into catheter 100 at a working tip 102. Silicon waveguides 104 are used for on-chip signal collection and communication as is described hereinabove. Optical signals obtained from the tissue are communicated to an extracorporeal unit 106 via optical fiber 108. The optical signal collected by system 10 is processed by extracorporeal unit 106 to identify cells of interest (e.g. malignant cells) in a tissue region scanned. Extracorporeal unit 106 can then guide the therapeutic unit to specifically treat such cells.

The nanoantennas of system 10 can be fabricated on a nanometric layer of a chemical substrate (for example on a water-soluble polymer such as vinyl alcohol polymer) which is delivered into the body. The formed nanoantennas can be released from the substrate at the site of treatment when exposed to physiological conditions (fluid, pH etc), physical pressure (exposure to ultrasound) and the like. When the nanoantennas of system 10 are released from the substrate they bind the targeted cell at maximum resolution of ~10 nm, governed by the chemical ligand and device dimensions.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Example 1

Plasmonic Signature of Different Mouse Tissues and Metastatic Melanoma (MM) Cells Sample Preparation
Mouse Tissues A 14 weeks old male mouse (C57B) was euthanized by overdose anesthetics. A variety of tissues were collected including: striated muscle, cardiac muscle, adipose tissue (retroperitoneal fat), liver, spleen, lung, adrenal, kidney. Each tissue was kept in a separate tube over ice water until analyzed. Tissue characterization for each sample was done at least twice (collected from separate mice).
Human MM Cells Two lines of human melanoma cells (Mel526, MEL624) (P 4-8), and human keratinocyte cells (P 4-8), representative of normal skin cells were cultured. The cell cultures were trypsinized, centrifuged at 3000 RPM, and the pellet was used for analysis.

Mouse MM Tumor Cells

A mouse from a melanoma model generated by using the RET proto-oncogene was euthanized and a subcutaneous lesion was excised from the mouse's back, kept in a tube over ice water until analysis. MM cells were identified within the analyzed tissue, well discriminated from the other cells and medium which occupied the bolus.

Plasmonic Analysis A commercially available scanning near field optical microscope (SNOM) was utilized for scanning the samples and to collect the reflected plasmonic waves. During each step, the plasmonic mode characteristics were extracted using spatial fast Fourier transform (s-FFT) and the plasmonic waveguide dispersion properties to create a plasmonic image. The intensity map of the image represents the amplitude of the plasmonic wave.

Results

Mouse Tissues

The results for the various mouse tissue examined are shown in FIGS. 5-10. The plasmonic waves at the center of the MIM waveguides as a function of the distance from the nanoantenna (L) are presented, with the wave amplitude is normalized to 0 dB. Different phase and plasmonic wavelength are observed for each examined tissue, enabling to differentiate different materials/signatures.

Human MM Cells

Figure 13:
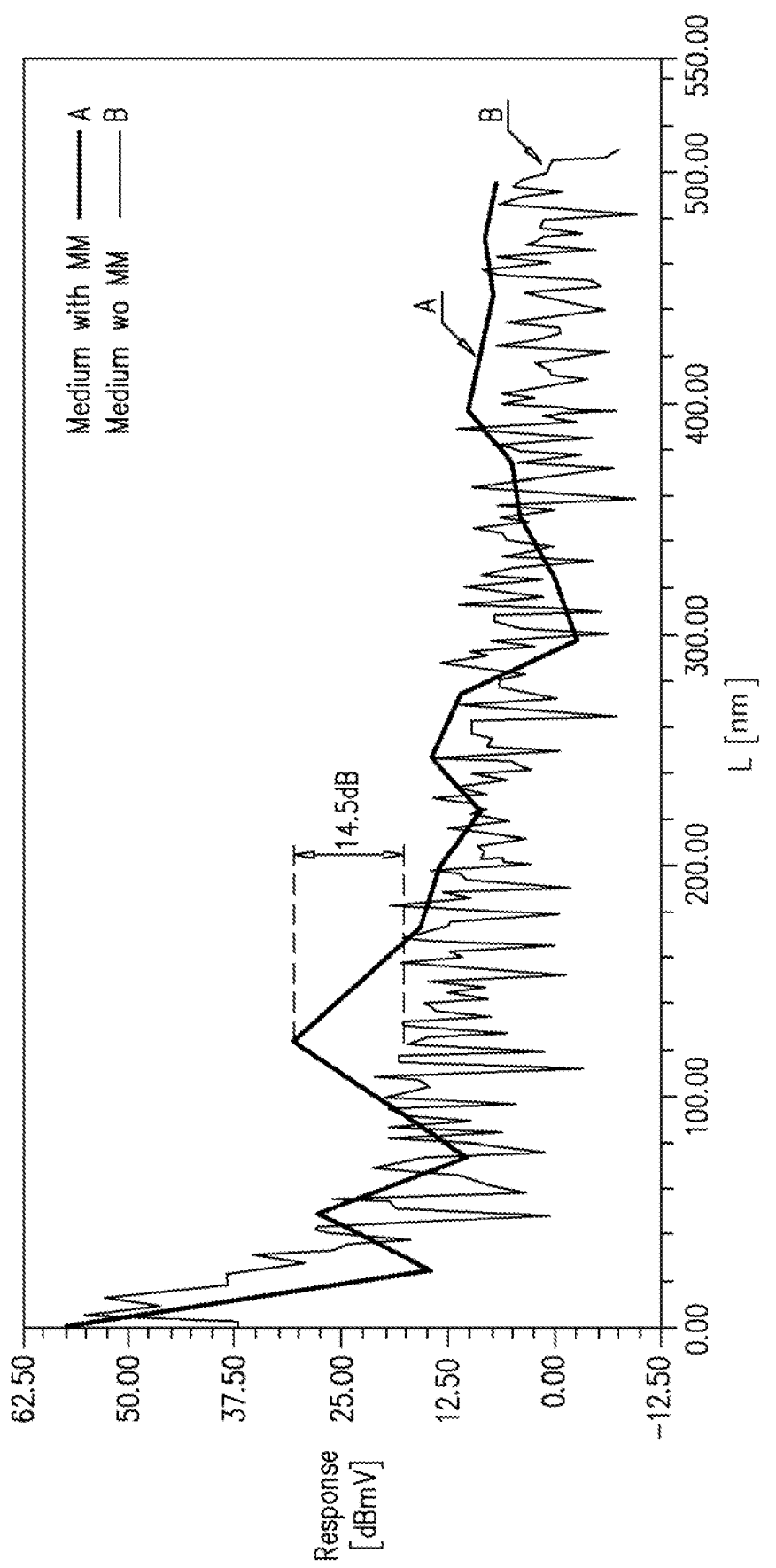
FIG. 13 is a graph showing the plasmonic peak of human MM cells in a sample including 5% human MM cells suspended in a growth medium.
Figure 15:
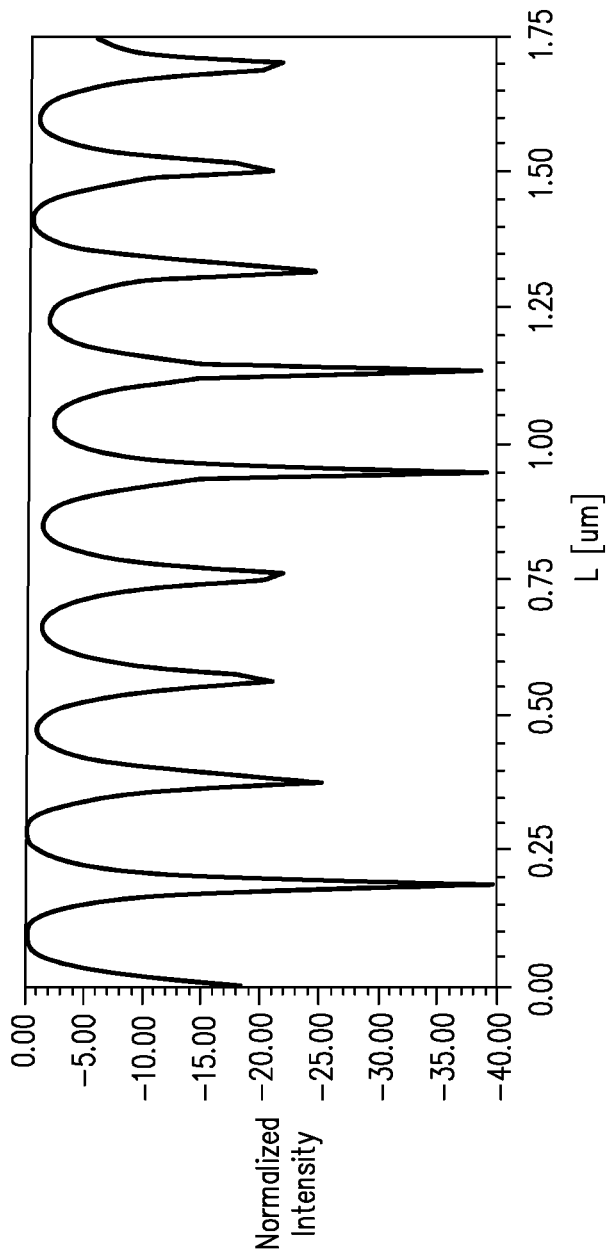
FIG. 15 is a graph showing the plasmonic profile of human skin keratinocytes.

Cultured human metastatic melanoma (MM) cells from both lines (Mel526, MEL624) yielded identical plasmonic characteristics. The human MM cell is represented by a plasmonic wavelength of 130 nm (horizontal axis at the graph of FIG. 1). The peak which represents the MM tissue (L=130 nm) is 14.5 dB higher compared with medium only. Thus, MM cells have a plasmonic signature at L=130 nm, which is 14.5 dB higher compared to the medium at the background (FIG. 13). Experiments were also performed on pellets including a mixture of MM cells and human skin keratinocytes (ratio 1:10) and MM cells and human skin keratocytes were identified based on their plasmonic signature (Keratinocyte signature shown in FIG. 15). Using the plasmonic information obtained for MM cells and keratocytes enables identification of these cell types in any sample by using, for example, spatial scanning approaches.

Mouse MM Cells

Figure 11:
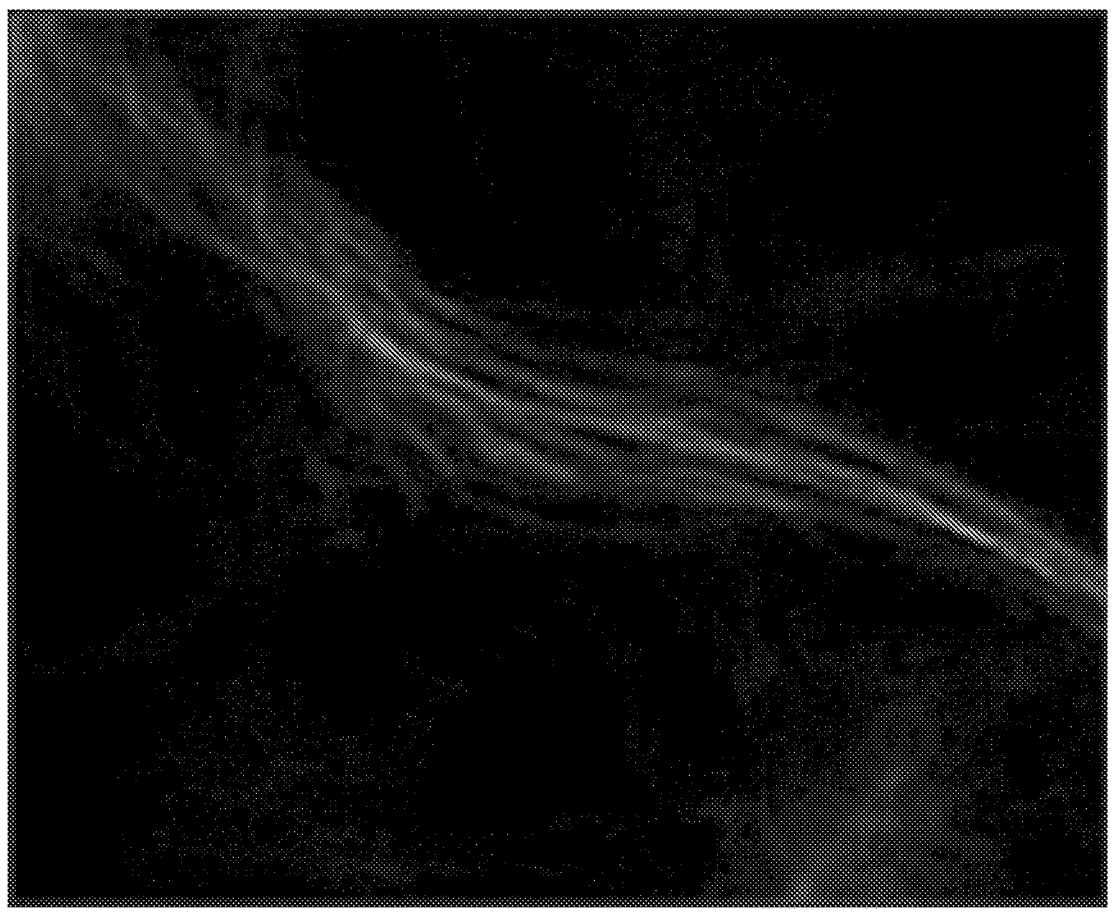
FIG. 11 illustrates plasmonic mapping of malignant melanoma (MM) tumor that was extracted from a mouse based on information obtained from analysis of human MM cells.

The MM regions in an engineered mouse were mapped based on the plasmonic signature obtained from human MM cells. FIG. 11 presents the results of plasmonic analysis of mouse MM tumor cells based on Human MM cells plasmonic data. The bright regions of this intensity map represent mouse MM cells while dark regions represent lack of mouse MM cells.

Figure 14:
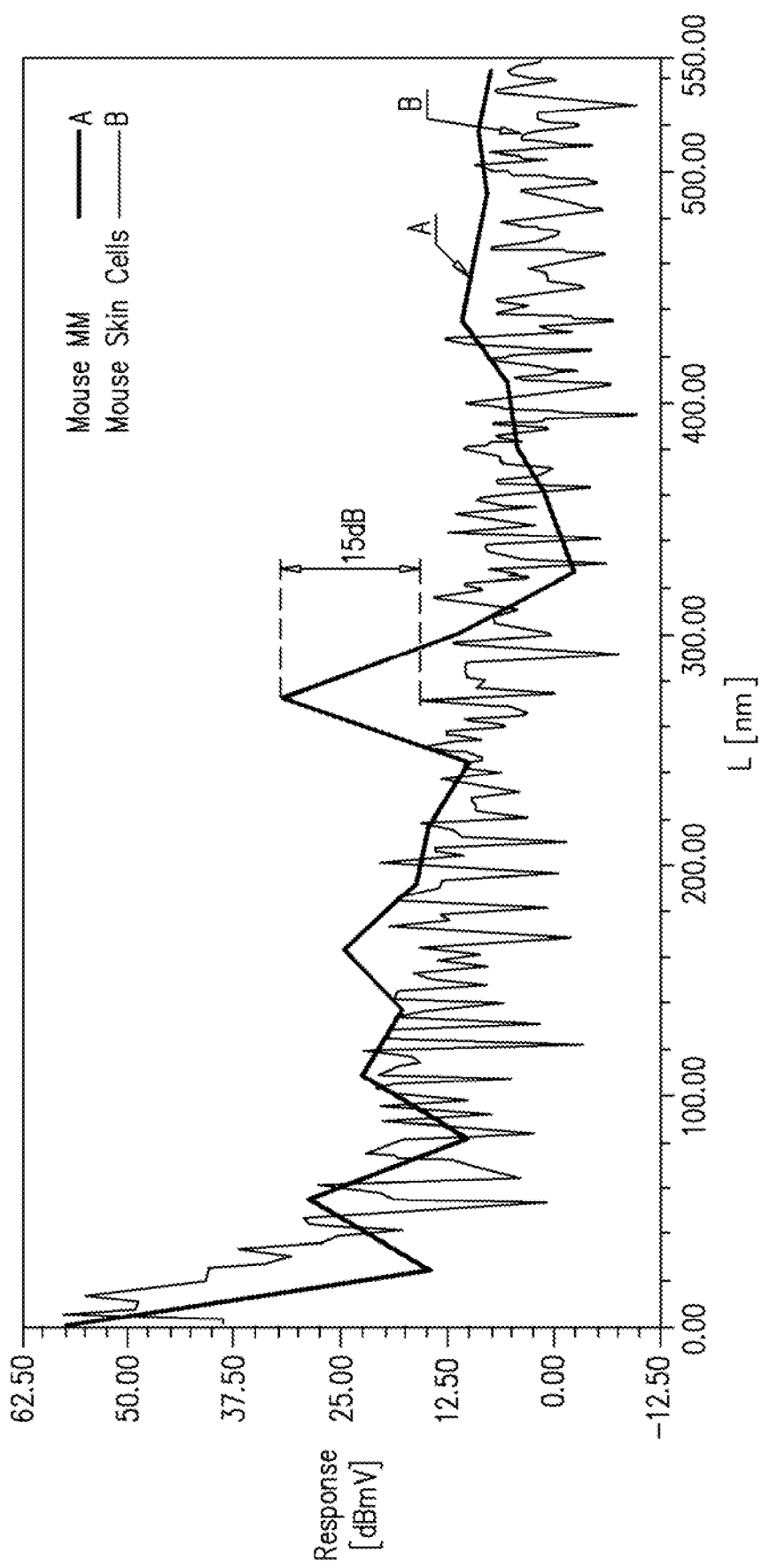
FIG. 14 is a graph showing the plasmonic peak of mouse MM cells (A line) infiltrating healthy Mouse skin cells (B line).

FIG. 14 illustrates the plasmonic peak obtained from a sample containing mouse MM tumor cells mixed with mouse skin cells. The peak which represents the MM tissue (L=130 nm) is 1.5 dB higher compared with skin cells.

Example 2

Plasmonic Signature of Human Metastatic Melanoma

The results presented above suggested that melanosomes are cell components responsible for the unique plasmonic signature of MM cell. Melanosomes in human MM cell culture were tagged with a fluorescent marker (Bruder et al. Melanosomal Dynamics Assessed with a Live-Cell Fluorescent Melanosomal Marker PLOS ONE August 2012) in order to ascertain their role in generating the plasmonic signature obtained herein. MM cells from both cell cultures were assessed, including cells with tagged and untagged melanosomes.

Materials and Methods

NUDE mice, 7 weeks old females were supplied by Harlan-Envigo, Israel, Human melanoma cells (Mel 526), at dose of 3×106 cells were injected subcutaneously. MM tumors were palpable after 3 weeks, and were excised surgically, as well as samples of normal skin.

Results

Figure 16:
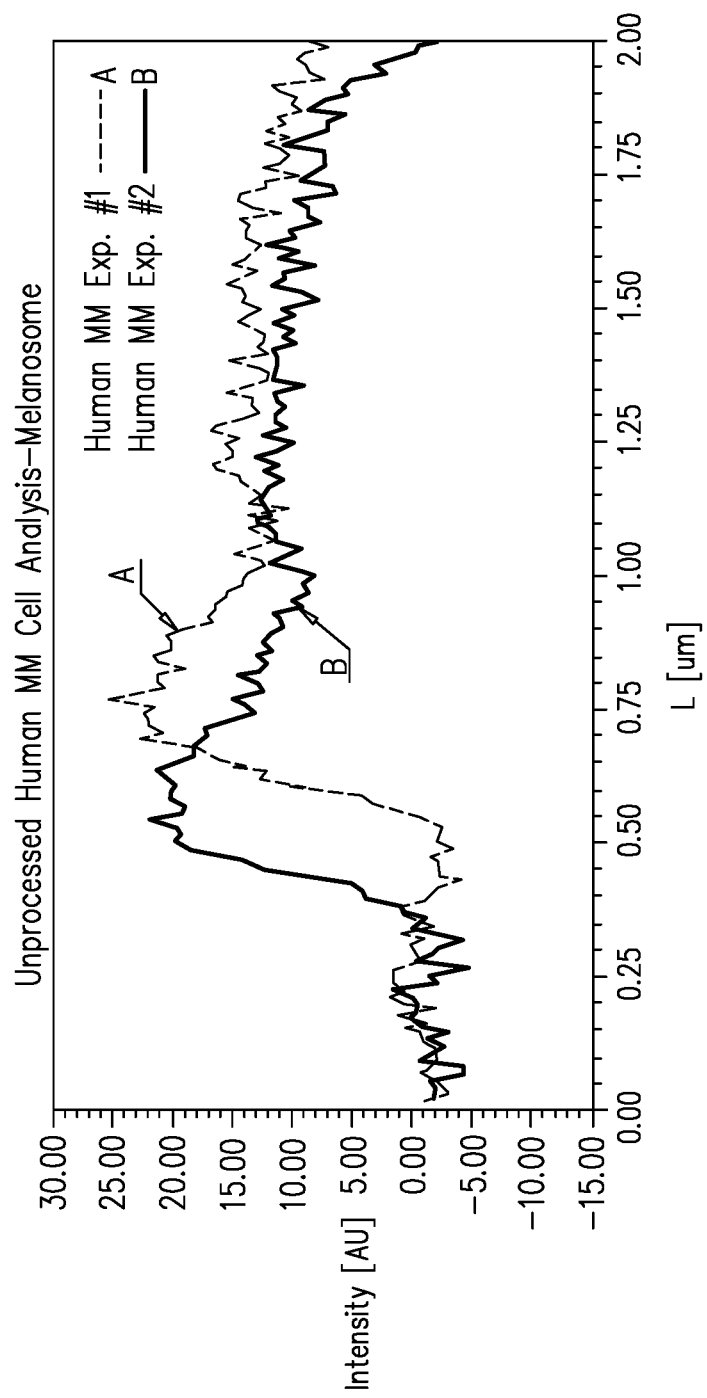
FIG. 16 is a graph showing human MM cells marked (B line) and unmarked (A line) with a fluorescent melanosomal marker.
Figure 17:
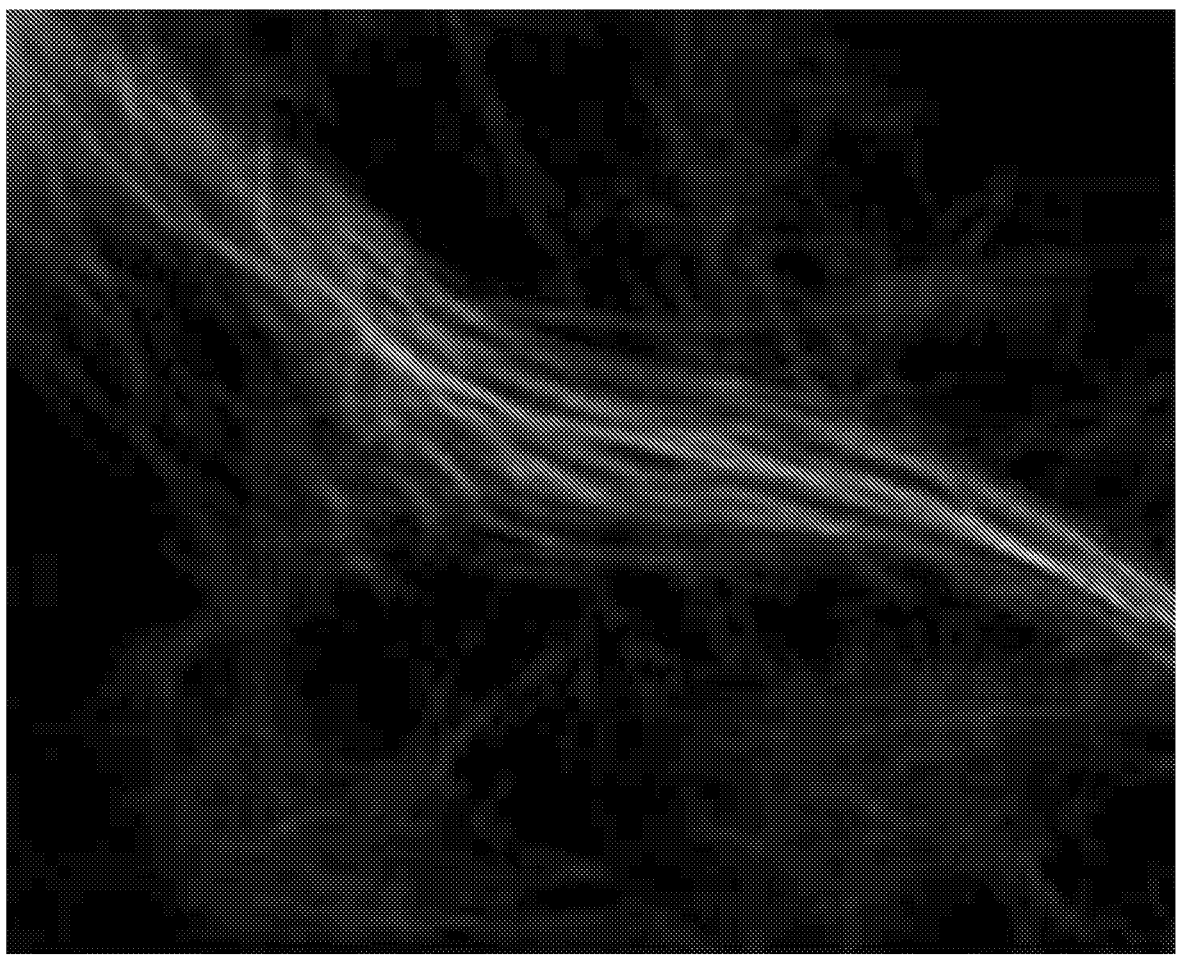
FIG. 17 illustrates plasmonic mapping of mouse tissue injected with human MM cells.
Figure 18:
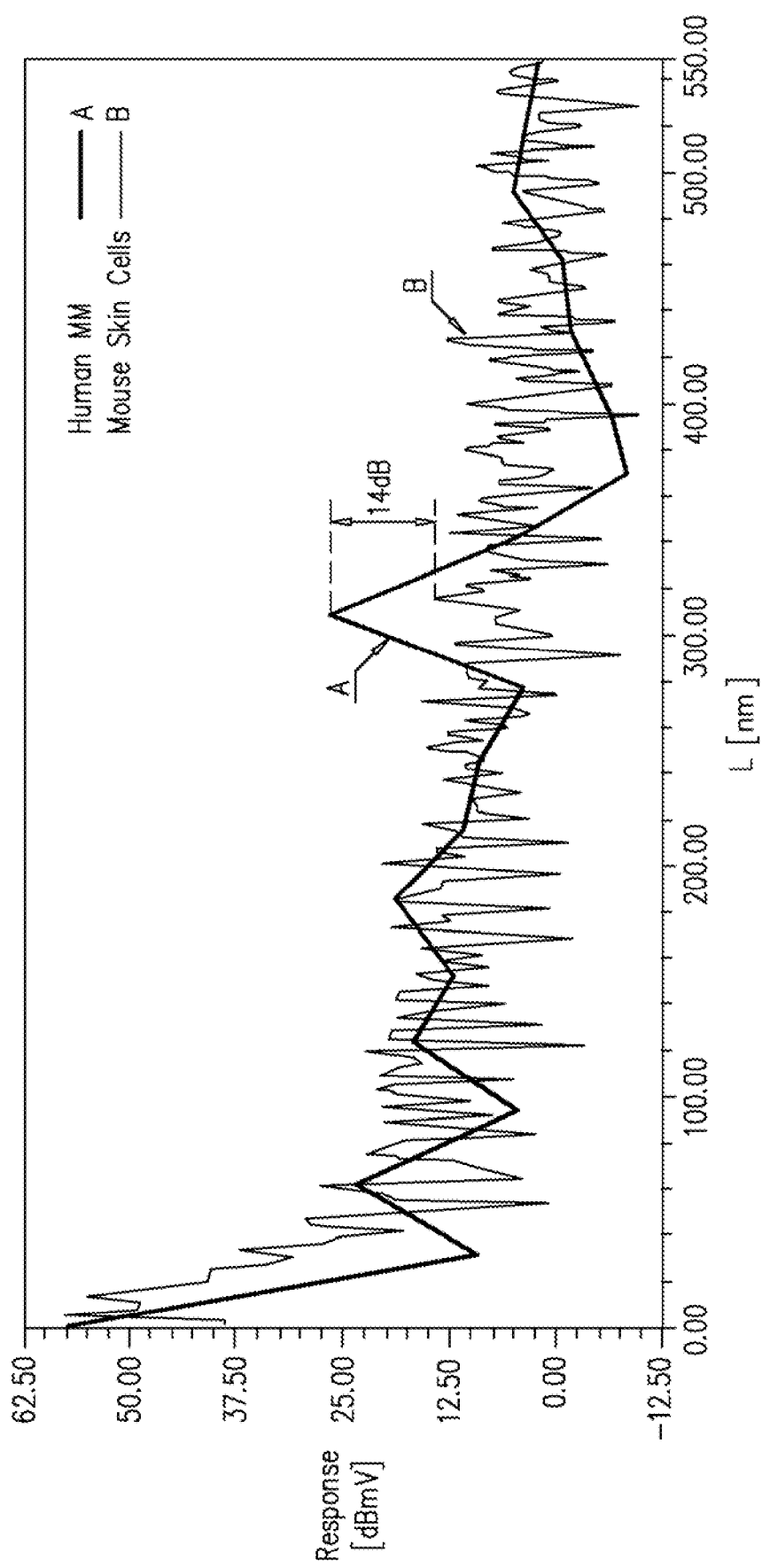
FIG. 18 is a graph illustrating detection of human MM cells (A line) over a background of mouse skin cells (B line).

FIGS. 16-18 illustrate the results obtained using the plasmonic approach of the present invention.

Several additional plasmonic thumb printing of Human Melanoma cells were obtained in lab experiments, with the cells suspended in medium in a petri dish. The samples were illuminated by an unfocused coherent He—Ne laser and the reflected light was collected and converted to plasmon polaritons by the nanoantenna. The Plasmonic Thumb Printing (profile) of a specific cell type was extracted after removal of the host-material effect. Samples of Human MM cells suspended in medium were tested as shown in FIG. 16. The analysis included two types of cell, with the first being an untreated Human MM Cells and the second is characterized by addition of phosphorous marking material attached to the cells' melanosomes. As observed, the two MM cell configurations exhibit distinguishable plasmonic signatures, thus providing further confirmation to the proficiency of the proposed system to distinguish nanoscale material and structural changes. FIG. 17 shows plasmonic imaging of human MM cells grown as a tumor in a NUDE, mouse, obtained by post processing the plasmon signatures obtained by the proposed invention. The figure is obtained via similar process to FIG. 11. The bright patterns represent the areas within the tested mouse, for which the signature correlation with isolated MM cells is higher than 80%. This imaging mechanism forms the basis for plasmon-correlation based imaging with sub diffraction optical resolution, FIG. 18 shows the specific plasmonic thumb printing of a human MM (A line) and a mouse skin (B line) cells on the same chart. The figure is obtained via similar process to FIG. 14. Similar to previous experiments detailed herein (FIG. 14), the plasmonic signature of the MM Cell exhibits different signature compared with that of regular skin cells, with less fluctuating character and a significant peak for plasmon wavelength of 300 nm.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A system for identifying biological material comprising:
   (a) a coherent light source for irradiating the biological material;
   (b) a device for collecting light waves reflected from the biological material and transforming said light waves to nanoplasmonic waves, the device comprising an array of nanoantennas coupled with respective plasmonic waveguides, each nanoantenna comprising at least two nanoantenna elements separated by a nanoscopic gap; and
   (c) a digital processor configured for extracting phase and amplitude information from said nanoplasmonic waves by performing spatial fast Fourier transform (s-FFT) on nanoplasmonic waves propagating inside said plasmonic waveguides to obtain a plasmonic signature of the biological material, and for identifying the biological material by comparing said phase and amplitude information to a database of plasmonic signatures.

2. The system of claim 1, wherein said coherent light source irradiates the biological material with a light having a wavelength in of 450 nm-10000 nm.

3. The system of claim 1, wherein at least one of said nanoantennas is fabricated from gold, silver or aluminum.

4. The system of claim 3, wherein at least one of said nanoantennas is coated with a 2 nm-5 nm protective layer fabricated from a polymer.

5. The system of claim 1, wherein at least one of said plasmonic waveguides is fabricated from a nanoplasmonic metal insulator-metal sandwich.

6. The system of claim 5, wherein at least one of said plasmonic waveguides includes an insulative layer of air, silicone oxide, a polymer or a ceramic.

7. The system of claim 1, wherein said phase and amplitude information is extracted at a spatial resolution of 10 nm-1000 nm.

8. The system of claim 1, further including a nano-metric phase shifter for controlling a phase of said light waves reflected from the biological material via electrostatic charging.

9. The system of claim 1, wherein said phase and amplitude information is utilized to identify and characterize the biological material.

10. The system of claim 1, wherein the biological material is selected from tissues, cells, subcellular structures, molecular structures, plaques and pathological organisms.

11. The system of claim 1, wherein the system is embedded within a catheter.

12. A method of identifying biological material comprising:
    (a) irradiating the biological material with coherent light;
    (b) collecting light waves reflected from the biological material and transforming said light waves to nanoplasmonic waves by a nanoplasmonic device comprising an array of nanoantennas coupled with respective plasmonic waveguides, each nanoantenna comprising at least two nanoantenna elements separated by a nanoscopic gap; and
    (c) extracting phase and amplitude information from said nanoplasmonic waves by performing spatial fast Fourier transform (s-FFT) on nanoplasmonic waves propagating inside said plasmonic waveguides, to obtain a plasmonic signature of the biological material; and
    (d) identifying the biological material by comparing said phase and amplitude information to a database of plasmonic signatures.

13. The method of claim 12, wherein said coherent light has a wavelength of 450 nm-10000 m.

14. The method of claim 12, further comprising scanning the biological material, wherein at each step of the scanning said phase and amplitude information is utilized to identify the biological material, thereby creating, a plasmonic mapping of the biological material.

* * * * *